(12) United States Patent
Seidl

(10) Patent No.: US 8,579,878 B2
(45) Date of Patent: Nov. 12, 2013

(54) HANGER LABEL FOR A LIQUID BAG AND METHOD FOR ATTACHING A LABEL TO A LIQUID-FILLED BAG

(75) Inventor: Peter Seidl, Munich (DE)

(73) Assignee: Schreiner Group GmbH & Co. KG, Oberschleissheim (DE)

( * ) Notice: Subject to any disclaimer, the term of this patent is extended or adjusted under 35 U.S.C. 154(b) by 0 days.

(21) Appl. No.: 13/453,323

(22) Filed: Apr. 23, 2012

(65) Prior Publication Data

US 2012/0283688 A1 Nov. 8, 2012

(30) Foreign Application Priority Data

May 2, 2011 (DE) .......................... 10 2011 100 156

(51) Int. Cl.
*A61M 5/14* (2006.01)
*B42D 15/00* (2006.01)

(52) U.S. Cl.
USPC .............. 604/408; 283/81; 283/101; 283/106

(58) Field of Classification Search
CPC ............ A61M 5/14; A61J 1/16; B42D 15/00; B65D 23/00; B65D 33/14; G09F 3/02
USPC ...................... 604/403–410; 40/638; 156/226; 215/12.1, 12.2, 200, 399; 281/2, 5; 283/81, 101, 106; 428/40.1, 41.7, 41.8, 428/41.9, 42.1–42.3
See application file for complete search history.

(56) References Cited

U.S. PATENT DOCUMENTS

| 6,082,777 | A  | * | 7/2000  | Grosskopf et al. ............... 283/81 |
| 6,457,747 | B1 | * | 10/2002 | Treleaven et al. ............... 283/81 |
| 2007/0235599 | A1 |   | 10/2007 | Seidl |
| 2010/0239190 | A1 | * | 9/2010  | McNamara et al. ............... 383/5 |

FOREIGN PATENT DOCUMENTS

| DE | 36 31 021 | 3/1988 |
| DE | 39 07 862 | 9/1990 |
| DE | 20 2006 005 907 | 6/2006 |

* cited by examiner

*Primary Examiner* — Philip R Wiest
*Assistant Examiner* — Benjamin Klein
(74) *Attorney, Agent, or Firm* — Collard & Roe, P.C.

(57) ABSTRACT

A special label is adapted for labeling of infusion bags containing a liquid. The bag is labeled only in a small partial area, which does not contain any liquid. For safe labeling capable of being automated, the label consists of a special film composite, which makes it possible to form a flap with special hinge properties. By virtue of the special fastening options, accidental detachment of the label from the infusion bag is prevented.

18 Claims, 3 Drawing Sheets

HANGER LABEL FOR A LIQUID BAG AND METHOD FOR ATTACHING A LABEL TO A LIQUID-FILLED BAG

CROSS REFERENCE TO RELATED APPLICATIONS

Applicant claims priority under 35 U.S.C. §119 of German Application No. 10 2011 100 156.9 filed May 2, 2011, the disclosure of which is incorporated by reference.

BACKGROUND OF THE INVENTION

1. Field of the Invention

The present invention relates to a label for a liquid-filled bag, as well as to a method for fastening such a label to a corresponding bag. In particular, the present invention relates to a label for a bag such as an infusion or transfusion bag, for example, wherein the label may be fixed as securely as possible to the bag, to ensure that safe hanging of the labeled bag is made possible.

2. The Prior Art

For the administration of special medications and pharmaceutical products, it may be necessary that an active substance is prepared in a liquid volume, for example a saline solution. This solution may then be administered to a patient by means of infusion. For this purpose, the ready-to-use solution must be filled into a container. For administration, this container is then hung in the proximity of the patient and the liquid passes through a tube with an infusion needle into the bloodstream of the patient.

Glass bottles and plastic bags are normally used as containers for such a pharmaceutical solution. For glass bottles, however, the danger then exists that they may be easily destroyed by mechanical stress. The risk of coming into contact with the prepared solution then exists for the treating person, which represents a great danger, for example, in the case of cytostatics. Moreover, the glass splinters of a broken glass bottle also represent a considerable risk of injury because of their sharp edges.

Therefore, plastic bags are being increasingly adopted for preparation of infusion solutions. In contrast to glass, however, the danger exists in plastic bags that certain chemical substances will be able to diffuse through the bag and so the pharmaceutical solution would become contaminated. This danger exists especially when a label is glued onto the bag for identification of a bag and then certain readily volatile components of the adhesive on the label diffuse through the bag. This phenomenon is known as adhesive migration.

Furthermore, the problem arises precisely for relatively small bags of identifying them to an adequate degree, since smaller bags necessarily also have a relatively small surface on which a label could be applied. On the other hand, a relatively elaborate and large area is necessary for identification of the medication with all required warning notices and documentation elements.

Further, due to the gluing of a label onto the usually transparent bag, the contents of the bag are concealed by the label. Thus contaminants that may be present or even abnormal discolorations of the contents may no longer be visually perceived and discovered.

For the reasons mentioned above, gluing a conventional label onto a bag is therefore associated with disadvantages and risks. On the other hand, the identification of an infusion bag may not be omitted. To the contrary, it is imperative in critical situations that a treating person be made familiar with the contents of the presented infusion bag in the shortest time possible and be able to check the contents carefully before the administration.

SUMMARY OF THE INVENTION

It is therefore an object of the present invention to provide, for the identification of such infusion bags, a label that on the one hand permits adequate identification of the bag and on the other hand avoids the problems mentioned above, such as adhesive migration or concealment of the contents, for example.

Moreover, it is an object of the present invention to permit labeling of an infusion bag with a label according to the invention efficiently and as automatically as possible.

This is accomplished by a label for a liquid-filled bag that comprises a first film, wherein the first film has an underside and an upper side coated at least partly with adhesive. The label further comprises a second film with an upper side and an underside, wherein the underside of the first film is bonded securely, at least partly, to the upper side of the second film, in order to form a film composite. The film composite of first film and second film possesses a punched cut having an open line contour with two end points, so that a strip-like flap is formed. The strip-like flap is joined to the rest of the film composite along an imaginary line between the two end points.

The invention further comprises a method for attaching a label to a liquid-filled bag, wherein the label is first received on a holding plate. Then the strip-like flap is raised and passed through an opening in the bag. Then, at least a partial area of the upper side of the first film is glued to at least a partial area of the bag. Further, the strip-like flap is glued to the bag.

It is a particular objective of the present invention to configure a two-layer film structure such that a flap is formed from the film composite. This flap may then be passed through a hanging opening of the bag and then folded back. By this special construction, it is sufficient that the film composite must be fastened only on an upper border of the bag for a secure hold. Since the region of this upper border is as a rule separated from the liquid reservoir located below it and thus does not contain any liquid, the danger of adhesive migration into the medication contained in the bag is therefore excluded. Further, since the label is applied only in a small partial area of the bag, the contents of the bag are not concealed and any contamination present may be recognized immediately.

For the labeling of a bag with the label according to the invention, it is advantageous that the strip-like flap has the tendency or the property of returning to the initial position. Thus, a kind of recovering hinge is formed. This effect is achieved by the fact that the film composite is formed from two individual film layers and furthermore suitable punched cuts are made at the point of the hinge. The special properties associated with the special flap are advantageous especially for the efficient and automated labeling of a bag, since on the one hand the flap has relatively high stiffness and on the other hand clearly defined pivoting out of the plane of the film is permitted by the hinge function.

In one embodiment, the underside of the first film is securely glued at least partly to the upper side of the second film. Thus a particularly stable film composite is obtained.

Preferably, a portion of the upper side of the second film is provided with an adhesive-repelling substance and the first film layer additionally comprises at least one further punched cut in the region that comes to lie on the second film layer. The first film comes to lie on the second film such that the further punched cut is located in the region of the adhesive-repelling substance. In this way, the film parts of the first film layer can be easily removed from the film composite and used as so-called auxiliary or additional labels for documentation purposes.

Preferably the film composite of first and second film has a punched cut for hanging the label. Thus, the bag may be easily hung at this opening on a suitable hanger device. Since the label is bonded very securely to the bag by virtue of the flap passed through the opening of the bag, the danger that the label will be detached from the bag in the hanging condition is almost excluded.

In a special embodiment, the first film has a first thickness and the second film has a second thickness, wherein the first thickness is greater than the second thickness. The recovery and hinge action of the flap may be achieved particularly well with this film composite.

Preferably at least the first film has at least one punched cut in the vicinity of the end point of the line contour of the strip-like flap. Thus, the hinge properties of the film composite are still further improved, which favors automated application of the label.

Preferably, at least the region of the upper side of the first film coated with adhesive is covered with a tape-like material. In a further preferred embodiment, a plurality of labels are applied onto a tape-like material and the tape-like material with the plurality of labels is wound onto a roll. Thus, the labels can be supplied in a particularly suitable form for further processing.

Preferably, the upper side of the first film is glued to the bag only in a region in which no liquid is present. Thus the danger of adhesive migration can be eliminated almost completely.

In one embodiment, the adhesive of the label is cured in yet a further step after gluing, so that a particularly secure bond between label and bag is formed after curing.

In a particular embodiment, the upper side of the first film is glued to the bag such that the glued strip-like flap is covered by a partial area of the first film. In this way, the flap is additionally fixed and a particularly reliable bond between label and bag is achieved.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
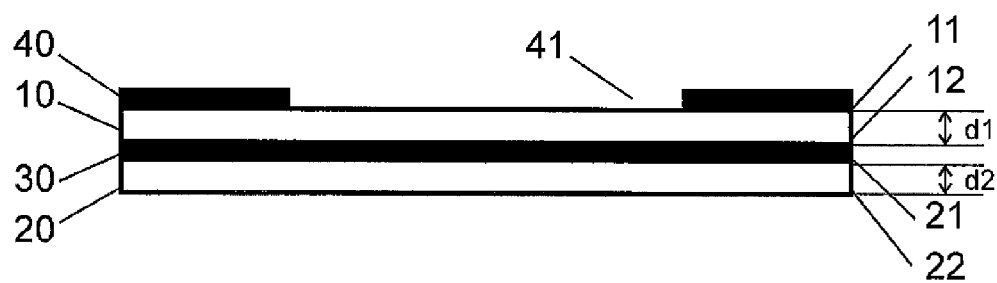
FIG. 1 shows a schematic cross section through a label according to the invention.
Figure 2:
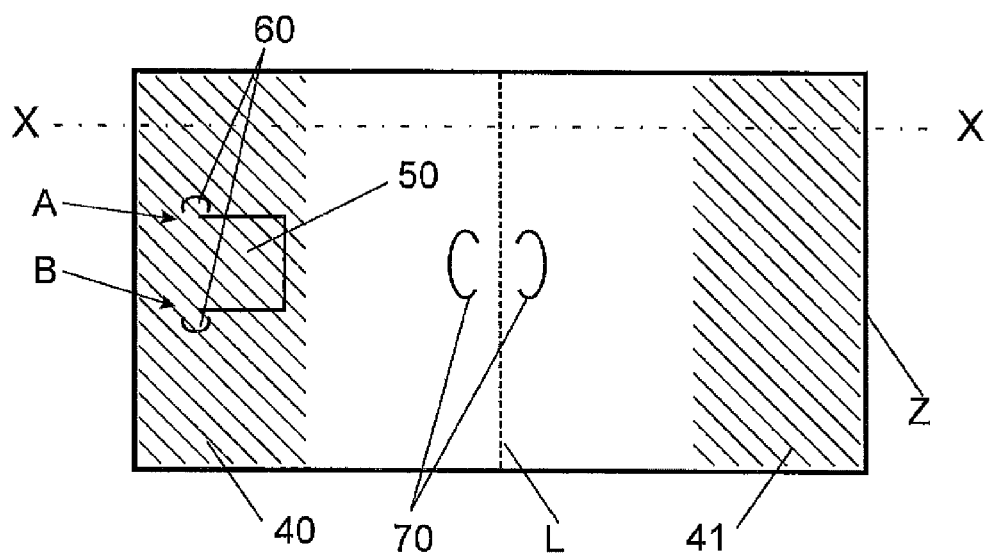
FIG. 2 shows a schematic top view of a label according to the invention.

Referring now in detail to the drawings, FIGS. 1 and 2 show schematic representations of a label 1 according to the invention. FIG. 2 shows a top view of this label 1 and FIG. 1 shows a cross section along section line X-X of FIG. 2.

This film composite comprises or consists of a first film layer 10 and a second film layer 20. The two film layers 10 and 20 are bonded securely to one another at least partially. For example, the underside 12 of the first film layer 10 and the upper side 21 of the second film layer 20 may be glued to one another with a suitable adhesive 30. However, other ways of bonding the two film layers to one another are also possible, especially laminating one film layer onto the other.

A tacky adhesive 40, 41 is applied on partial areas of the upper side 11 of the first film layer 10. For example, this tacky adhesive 40, 41 may be imprinted on the upper side 11 of the first film layer 10 in a printing method.

As illustrated in FIG. 2, a strip-like flap 50 is punch-cut into the label. This flap 50 is formed by a punched cut in the form of an open line contour between the end points A and B. This punched cut for the flap 50 passes through both films 10 and 20. Thus a hinge between the flap 50 and the rest of label 1 is formed along an imaginary line between points A and B.

Furthermore, one or more punched cuts 60 are made in the upper film layer 10 in the vicinity of the end points A and B of the flap 50. These punched cuts 60 are matched in shape and size to the desired hinge properties and thus contribute substantially to the improvement of the hinge function. In particular, during expulsion of the flap 50 from the film composite, the flap has the tendency to return to its original position.

In the left region of the label 1, an adhesive 40, 41 is also applied on the upper side 11 of the upper film layer 10. In particular, the adhesive is also applied in the region of the flap 50.

Furthermore, the label 1 may also have punched cuts 70 having an open or closed line contour. These punched cuts 70 are configured such that they serve as hanging openings. The punched cuts 70 pass through both film layers 10 and 20. Thus it is possible, for example, to pass a hook through the opening and hang label 1 together with the labeled bag thereon.

In a special embodiment, especially the first film layer 10 can comprise yet further punched cuts 80, by which the partial areas of the first film layer 10 are separated. These partial areas 81, 82 and 83 thus separated may serve as removable auxiliary or documentation labels, which may be removed at a later time and, for example, pasted into the patient's record. For better illustration, in FIG. 3, hatching 40 for indication of the adhesive application is not extended into areas 81 to 83. Nevertheless, the auxiliary or documentation labels are provided with an adhesive 40 on their underside.

For detachment of these additional partial labels 81, 82 and 83, it is then advantageous when upper side 21 of second film layer 20 is provided with an adhesive-repelling coating 90 in the region of the partial labels. For example, a silicone treatment may be imprinted on upper side 21 for this purpose. Thus the individual partial labels can be easily removed. Adhesive 30 between first film layer 10 and second film layer 20, more accurately on the underside 12 of the first film layer, then simultaneously serves as adhesive for subsequently pasting the partial labels 81, 82, 83 into a patient record or the like.

After manufacture of such a label, at least the area on upper side 11 of first film layer 10 provided with adhesive 40, 41 may be provided with a covering film and thus protected. In particular, a so-called liner, which has an adhesive-repelling coating on the side facing adhesive 40, 41, is suitable for this purpose.

Preferably, a plurality of labels according to the invention is disposed side-by-side on such a tape-like liner. Thus the tape-like liner with the labels may be simply rolled up and supplied for further processing.

Figure 4:
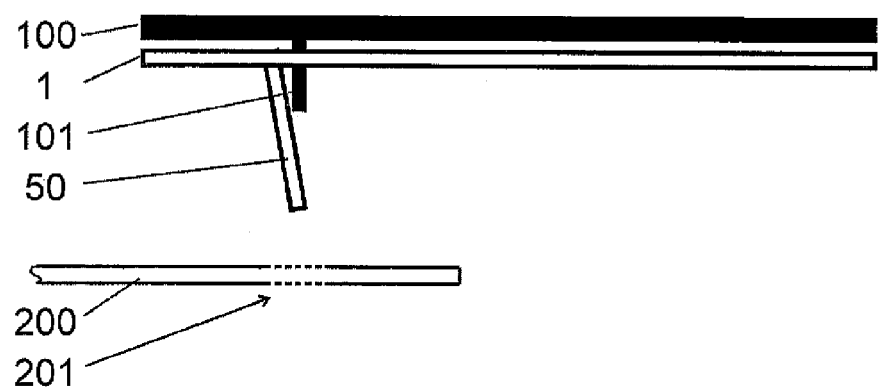
FIG. 4 shows a schematic representation of a label as it has been received by an application plate.

For the labeling of an infusion bag with such a label, an individual label may first be removed from the liner. For example, the label may be detached with a suction plate. FIG. 4 shows such a plate 100, on the underside of which a label 1 according to the invention is held by suction.

Plate 100 further possesses a pin 101 or the like. Upon reception of label 1 on plate 100, pin 101 presses flap 50 out of the plane of the film. Ideally, flap 50 is then positioned almost perpendicularly, as illustrated by way of example in FIG. 4. However, a different angle of orientation of flap 50 is also entirely acceptable.

Figure 3:
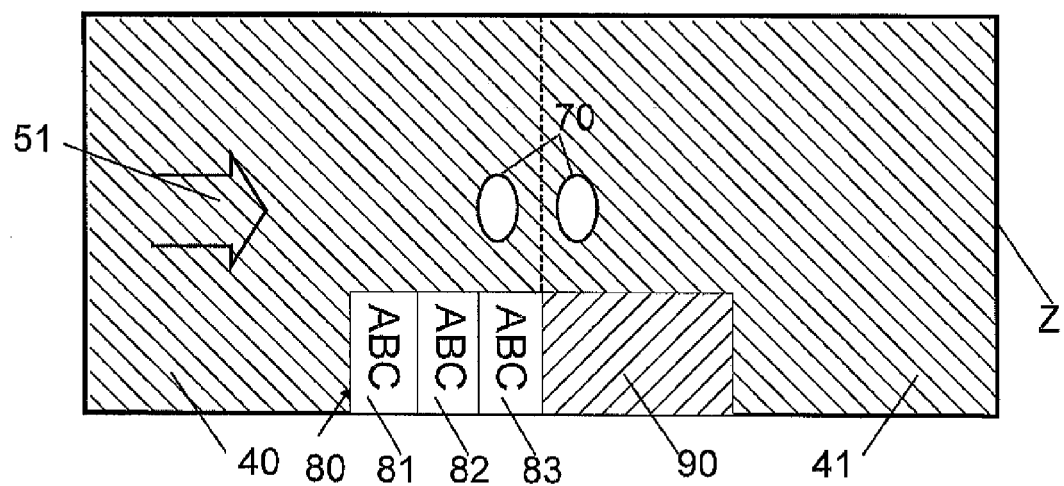
FIG. 3 shows a further schematic top view of a label according to the invention.

For the passage of flap 50 through an opening in the bag, it is then particularly advantageous when a tip is formed at the raised end of the flap. For example, the free end of flap 51 may have an arrowhead shape, as illustrated in FIG. 3.

Further, it has proved advantageous when two films with different thickness are used for the structure of the film composite. Particularly good hinge properties are then obtained when the film for first film layer 10 has a greater thickness d1 than the film for second film layer 20. Film composites in which the first film layer has a thickness d1 of 100 to 200 micrometers are very suitable for this. Films with a thickness d2 between 36 and 100 micrometers have proved to be suitable for the second film layer.

Films of polyester can be used for both film layers. However, even film composites, in which one or two film layers consist of a different material, are entirely possible.

By virtue of the two-layer film composite and also of the additional punched cuts 60, a hinge is formed at the end of the flap joined to the rest of the label. In contrast, flap 50 itself has sufficient stiffness and retains its shape even during expulsion of the flap from the plane of the film. Because of the special two-layer configuration and/or the additional punched cuts 60, flap 50 can be expelled in well-defined manner and thus automatic further processing is made possible.

A label with raised flap 50 as prepared above may now be attached to an infusion bag 200. For this purpose label 1 located on the plate 100 is brought together with bag 200 such that expelled flap 50 is passed through a hanging opening 201 of the bag 200. Then flap 50 is folded back into its original position onto the side of bag 200 disposed opposite the label. In a subsequent step, label 1 is folded around an imaginary line L and in this way the second end region Z, which lies opposite the first end region already glued to the bag 200, likewise comes to lie on the bag.

In this embodiment, second end region Z is also coated with adhesive 41. Alternatively, the label may be coated with adhesive over its entire surface. Thus second end region Z is also glued to the border of bag 200. Flap 50 is then covered by the second end region of the label and flap 50 and the second end region are glued to one another.

Because of the gluing of second end region Z to the bag, the flap 50 is additionally fixed and slipping-out of the flap 50 is thus reliably prevented. Thus a particularly secure bond between bag 200 and label 1 is achieved.

After the curing of adhesive 40, therefore, bag 200 and label 1 are securely bonded to one another. This curing of the adhesive may be activated or accelerated by irradiation with infrared or ultraviolet light. Any further type of activation or acceleration of curing of the adhesive is likewise possible.

Figure 5:
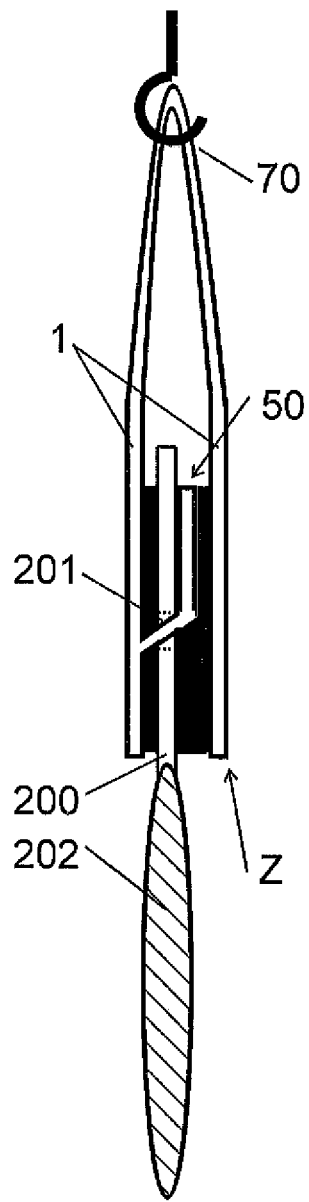
FIG. 5 shows a schematic representation of the cross section of a label that has been bonded to a liquid bag.

FIG. 5 shows, in cross section, an infusion bag 200 to which a label 1 according to the invention as described above has been attached. The infusion bag comprises a hanging portion 200 in the upper part and a liquid reservoir 202 in the lower part. The upper hanging portion 200 is constructed such that no liquid can be present therein. This may be achieved, for example, by suitable heat-sealing of the plastic films in this region. The infusion liquid is therefore present only inside the lower liquid reservoir 202.

In this case, adhesive 40 of the label comes into contact with the infusion bag only in hanging region 200, where no liquid is present. In contrast, the region of liquid reservoir 202 of the bag does not come into contact with adhesive, so that the danger of adhesive migration can be avoided. As illustrated in FIG. 5, flap 50 is passed through the original hanging opening 201 of bag 200 and glued to the folded-over part of the label on the side opposite the label. In this way particularly secure fastening of infusion bag 200 with label 1 is achieved. Thereby the risk that the label will become accidentally detached from the bag may be almost excluded.

In summary, the invention relates to a special label for the labeling of infusion bags containing a liquid. The bag is labeled only in a small partial area, which does not contain any liquid. For safe labeling capable of being automated, the label consists of a special film composite, which makes it possible to form a flap with special hinge properties. By virtue of the special fastening options, accidental detachment of the label from the infusion bag may be almost excluded. In this connection, embodiments with additional removable labels are possible.

Accordingly, while only a few embodiments of the present invention have been shown and, described, it is obvious that many changes and modifications may be made thereunto without departing from the spirit and scope of the invention.

What is claimed is:

1. A label for a liquid-filled bag, comprising:
a first film with an upper side coated at least partially with adhesive and an underside; and
a second film with an upper side and an underside;
wherein the underside of the first film is securely bonded, at least in partial regions, to the upper side of the second film, in order to form a film composite having an edge,
wherein the film composite possesses a punched cut having an open line contour with two end points, so that a strip-like flap configured to be passed through an opening in the bag and configured to be glued to a folded back part of the label, is formed and the strip-like flap is bonded to the rest of the film composite along a line between the two end points,
wherein the punched cut is distant from the edge of the film composite, and
wherein the film composite possesses a first further punched cut and a second further punched cut each being one of an open and a closed line contour for hanging the label.

2. The label according to claim 1, wherein the underside of the first film is bonded to the second film via glue.

3. The label according to claim 1, wherein a portion of the upper side of the second film is provided with an adhesive-repelling substance and the first film comprises a further punched cut, wherein the first film comes to lie on the second film such that the further punched cut is located in a region of the adhesive-repelling substance.

4. The label according to claim 1, wherein the first film has a first thickness and the second film has a second thickness, and wherein the first thickness is greater than the second thickness.

5. The label according to claim 1, wherein a surface of the first film coated with adhesive is covered with a tape-like material.

6. The label according to claim 1, wherein the label has at least one additional punched cut in the vicinity of each of the end points of the line contour of the punched cut of the strip-like flap, in order to allow the flap, after expulsion from the film composite, to return to its original position again.

7. A method for attaching a label to a liquid-filled bag, the label comprising a first film with an upper side coated at least partially with adhesive and an underside and a second film with an upper side and an underside, the underside of the first film being securely bonded, at least in partial regions, to the upper side of the second film, in order to form a film composite, the film composite possessing a punched cut having an open line contour with two end points, so that a strip-like flap is formed and the strip-like flap is bonded to the rest of the film composite along a line between the two end points, which method comprises the following steps:
- receiving the label;
- raising the strip-like flap;
- passing the strip-like flap through an opening in the bag;
- gluing at least a partial area of the upper side of the first film to at least a partial area of the bag; and
- folding back of raised strip like flap.

8. The method according to claim 7, wherein the upper side of the first film is glued to the bag only in a region in which no liquid is present.

9. The method according to claim 7, wherein the upper side of the first film is glued to the bag such that the folded-back strip-like flap is covered by a partial area of the first film.

10. The method according to claim 7, further comprising the step of curing the adhesive.

11. An infusion bag to which a label is attached, the label comprising:
- a first film with an upper side coated at least partly with adhesive and an underside; and
- a second film with an upper side and an underside;
- wherein the underside of the first film is securely bonded, at least in partial regions, to the upper side of the second film, in order to form a film composite; and
- wherein the film composite possesses a punched cut having an open line contour with two end points, so that a strip-like flap is formed and the strip-like flap is bonded to the rest of the film composite along a line between the two end points, and
- wherein the strip-like flap is passed through an opening in the bag and is glued to a folded-back part of the label.

12. The infusion bag according to claim 11, wherein the underside of the first film is bonded to the second film via glue.

13. The infusion bag according to claim 11, wherein a portion of the upper side of the second film is provided with an adhesive-repelling substance and the first film comprises a further punched cut, wherein the first film comes to lie on the second film such that the further punched cut is located in the region of the adhesive-repelling substance.

14. The label for a liquid-filled bag according to claim 13, wherein the label has a rectangular outer contour, wherein the punched cut forming the strip-like flap, the further punched cut comprised in the first film, and first and second further punched cuts for hanging the label are all disposed within the rectangular outer contour of the label.

15. The infusion bag according to claim 11, wherein the film composite has at least one further punched cut for hanging the label.

16. The infusion bag according to claim 11, wherein the first film has a first thickness and the second film has a second thickness, and wherein the first thickness is greater than the second thickness.

17. The infusion bag according to claim 11, wherein a surface of the first film coated with adhesive is covered with a tape-like material.

18. The infusion bag according to claim 11, wherein the label has at least one additional punched cut in the vicinity of each of the end points of the line contour of the punched cut of the strip-like flap, in order to allow the flap, after expulsion from the film composite, to return to its original position again.

\* \* \* \* \*